United States Patent
Vilsmeier et al.

(10) Patent No.: US 7,787,932 B2
(45) Date of Patent: Aug. 31, 2010

(54) PLANNING AND NAVIGATION ASSISTANCE USING TWO-DIMENSIONALLY ADAPTED GENERIC AND DETECTED PATIENT DATA

(75) Inventors: Stefan Vilsmeier, Kufstein (AT); Mario Zeiss, Tokyo (JP); Claus Schaffrath, München (DE); Thomas Feilkas, Grafing (DE)

(73) Assignee: BrainLAB AG, Feldkirchen (DE)

( * ) Notice: Subject to any disclaimer, the term of this patent is extended or adjusted under 35 U.S.C. 154(b) by 786 days.

(21) Appl. No.: 10/811,330

(22) Filed: Mar. 26, 2004

(65) Prior Publication Data

US 2005/0004451 A1    Jan. 6, 2005

Related U.S. Application Data

(63) Continuation-in-part of application No. 10/133,867, filed on Apr. 26, 2002, now Pat. No. 7,194,295.

(60) Provisional application No. 60/494,935, filed on Aug. 13, 2003.

(30) Foreign Application Priority Data

Mar. 26, 2003    (EP) ................. 03 006 782

(51) Int. Cl.
*A61B 5/05*  (2006.01)
*G06K 9/00*  (2006.01)
*G06K 9/34*  (2006.01)
*G06K 9/46*  (2006.01)

(52) U.S. Cl. .............. 600/424; 600/416; 600/425; 382/128; 382/154; 382/173; 382/190

(58) Field of Classification Search ............ 600/407, 600/424, 425, 427, 429; 606/130; 378/16, 378/207; 382/128, 154, 173, 190

See application file for complete search history.

(56) References Cited

U.S. PATENT DOCUMENTS 5,799,055 A    8/1998  Peshkin et al.

(Continued)

FOREIGN PATENT DOCUMENTS

DE    196 39 615    9/1996

(Continued)

OTHER PUBLICATIONS

La thèse de doctorat de Markus Fleute, Oct. 3, 2001, "Shape Reconstruction for Computer Assisted Surgery based on Non-rigid registration of statistical models with intra-operative point data and X-ray images".

(Continued)

*Primary Examiner*—Eirc F Winakur
*Assistant Examiner*—Michael T Rozanski
(74) *Attorney, Agent, or Firm*—Renner, Otto, Boisselle & Sklar, LLP

(57) ABSTRACT

A method for computer-assisted medical navigation and/or pre-operative treatment planning includes detecting the current position of a patient or a part of a patient's body and the positions of medical treatment devices or treatment-assisting devices. The detected positional data can be assigned to body structure data, in order to jointly use the body structure data in assignment with the positional data, within the context of assisting the treatment. The body structure data can be used which is obtained based on a three-dimensional generic model, where the model is adapted by two-dimensional data linking with patient-characteristic, two-dimensional detection data.

22 Claims, 6 Drawing Sheets

U.S. PATENT DOCUMENTS

| | | | |
|---|---|---|---|
| 5,954,648 A * | 9/1999 | Van Der Brug | 600/411 |
| 6,033,415 A | 3/2000 | Mittelstadt et al. | |
| 6,125,164 A | 9/2000 | Murphy | |
| 6,470,207 B1 * | 10/2002 | Simon et al. | 600/426 |
| 6,711,432 B1 * | 3/2004 | Krause et al. | 600/427 |
| 7,194,295 B2 * | 3/2007 | Vilsmeier | 600/416 |
| 2003/0185346 A1 | 10/2003 | Vilsmeier | |
| 2005/0004451 A1 | 1/2005 | Vilsmeier et al. | |
| 2005/0015003 A1 | 1/2005 | Lachner et al. | |

FOREIGN PATENT DOCUMENTS

| | | |
|---|---|---|
| DE | 196 39 615 | 4/1998 |
| DE | 100 47 314 | 4/2001 |
| DE | 100 37 491 | 2/2002 |
| EP | 1 348 393 | 3/2002 |
| EP | 1222636 | 7/2002 |
| FR | 2 810 769 | 6/2000 |
| WO | 99/59106 | 11/1999 |
| WO | 01/22368 | 3/2001 |
| WO | WO 01/22368 | 3/2001 |
| WO | 01/78015 | 10/2001 |
| WO | 02/062249 | 8/2002 |
| WO | WO 02/062249 | 8/2002 |

OTHER PUBLICATIONS

La thèse de doctorat de Sébastien Laporte, Dec. 17, 2002, "reconstruction 3D du squelette humain pour la biomécanique par radiographic biplane à dose minimale d'irradiation".

"Reconstruction 3D des os du genou par rétroprojections radiographiques multiplanes", Gargouri at al., 1° symposium de biomatériaux avancées, Oct. 2-5, 1997, Montréal.

"3D reconstruction method using non stereo-corresponding 2D contours on X-rays: case of the femur" Laporte et al., International Society of Biomechanics, XVIIIth Congress, Jul. 8-13, 2001, Zurich.

Opposition against corresponding EP Application No. 02 007 218.7 dated Dec. 18, 2007.

Messmer, et al., "Volumetric model determination of the tibia based on 2D radiographs using a 2D/3D database", Computer Aided Surgery, vol. 6, pp. 183-194.

Benameur et al., "3D Biplanar Reconstruction of Scoliotic Vertabrae Using Statistical Models", IEEE International Conference on Computer Vision and Pattern Recognition, CVPR'01, vol. II, pp. 577-582.

Decision and Minutes of the Oral Proceedings, EP Application No. 02007218, dated Nov. 26, 2009, including relevant Opposition documents and cited references.

Statement of Grounds of Appeal, EP Application No. 03006782.1 dated Nov. 27, 2009, including relevant Appeal documents and cited references.

Lotjonen; "Reconstruction of 3-D Geometry Using 2-D Profiles and a Geometric Prior Model"; Oct. 1999.

IEEE Computer Society Conference; "Computer Vision and Pattern Recognition"; Dec. 2001.

Laporte et al.; "3D reconstruction method using non stereo-corresponding 2D-contours on X-rays: case of the femur.", 2006.

Wikipedia; "X-ray computed tomography"; Oct. 2009.

Decision and Minutes of the Oral Proceedings, EP Application No. 02007218, dated Feb. 8, 2010, including relevant Opposition documents and cited references.

Delorne et al., "Three-Dimensional Modelling and Rendering of the Human Skeletal Trunk from 2D Radiographic Images", IEEE, 1999, pp. 497-505.

Jacobson, "Facial Analysis in Two and Three Dimensions", Chapter 21, pp. 273-295, 1995.

Russakoff et al., "Fast calculation of digitally reconstructed radiographs using light fields", Proceedings of SPIE, vol. 5032, 2003, pp. 684-695.

Wikipedia; "Digital rekonstruiertes Röntgenbild"; Oct. 2009.

Opposition against corresponding European Application No. 03 006782.1.

Fleute, Markus, "Shape Reconstruction for Computer Assisted Surgery based on Non-Rigid Registration of Statistical Models with Intra-Operative Point Data and X-ray Images", Oct. 2001.

Gargouri, I., et al., "Reconstruction 3D des os du genou par rétroprojections radiographiques multiplanes", École de Technologie Supérieure, Montréal, Québec, Canada, 1997.

Laporte, "3D reconstruction method using non stereo-corresponding 2D-contours on X-rays: case of the femur", Orthopaedic Biomechanics & Rehabilitation I, 2006.

* cited by examiner

PLANNING AND NAVIGATION ASSISTANCE USING TWO-DIMENSIONALLY ADAPTED GENERIC AND DETECTED PATIENT DATA

RELATED APPLICATION DATA

This application is a continuation-in-part of U.S. application Ser. No. 10/133,867, filed on Apr. 26, 2002, now U.S. Pat. No. 7,194,295 and claims priority of U.S. Provisional Application No. 60/494,935 filed on Aug. 13, 2003, which is incorporated herein by reference in its entirety.

FIELD OF THE INVENTION

The present invention relates to a method and device for computer-assisted medical navigation and/or pre-operative treatment planning. In particular, it relates to a method and device for planning and navigation assistance using two-dimensionally adapted and detected patient data.

BACKGROUND OF THE INVENTION

Computer-assisted, stereotactic systems, which work with the aid of body structure data obtained from tomographic detection systems and with the assistance of x-ray images produced in situ are known, for example, from U.S. Pat. Nos. 4,791,934 and 5,799,055. X-ray imaging used to assist in operations is discussed in U.S. Pat. Nos. 5,967,982, 5,772,594 and 5,784,431.

Referencing the current position of the structures to be operated on by means of pre-operatively produced three-dimensional patient data and x-ray images produced in situ (fluoro-CT matching) is introduced here as a non-contact method, which is therefore suitable for minimally invasive surgery.

Where accurate medical navigation is to be provided, the prior art still works with the aid of body structure data originating from tomographic detection systems, such as, for example, computer tomography devices or nuclear spin tomography devices. The patient to be treated is thus positionally registered in situ with respect to the image data determined beforehand. Operating instruments are then virtually displayed in the same relation to the image data as to the actual patient, to make the body structure data or, if possible, also x-ray image data useful to the surgeon in the operating room.

Disadvantages of such methods, in which tomographs (CT, MR) or x-ray images are produced, especially for navigating within the framework of treatment, include the radiation load on the patient and the high costs, since such devices are very expensive both to purchase and to maintain and operate.

Attempts have been made to develop systems that may be employed without body structure data separately detected beforehand, for example, based on statistical models of image data sets for body structures. However, such systems lack the required accuracy for the respective patient to be treated.

DE 100 37 491 A1 and WO 99/59106 describe methods for providing 3D information with the aid of fluoro-images. The starting point in all methods is recording transillumination images of the patient or of the desired structure. A localization system is used to obtain spatial information using the images. DE 100 37 491 A1 initially uses two fluoro-images, from which to reconstruct a rough 3D model. Other images from different angles are used to specify the model more precisely. In accordance with WO 99/59106, at least three fluoro-images of the patient are generally made. These are anterior-posterior, lateral and anterior-posterior with the head inclined backwards. In addition to the transillumination images, photographs of the patient are also used. In this prior art, the model is painstakingly adapted in three-dimensional space.

SUMMARY OF THE INVENTION

In accordance with one aspect of the invention, a method for computer-assisted medical navigation or pre-operative treatment planning can include detecting a position of a patient or a part of a patient's body and detecting positions of medical treatment devices or treatment-assisting devices. The method can further include assigning the detected positions to body structure data, the body structure data being obtained from a three-dimensional generic model.

BRIEF DESCRIPTION OF THE DRAWINGS

These and further features of the present invention will be apparent with reference to the following description and drawings, wherein.

DETAILED DESCRIPTION OF THE INVENTION

Figure 1:
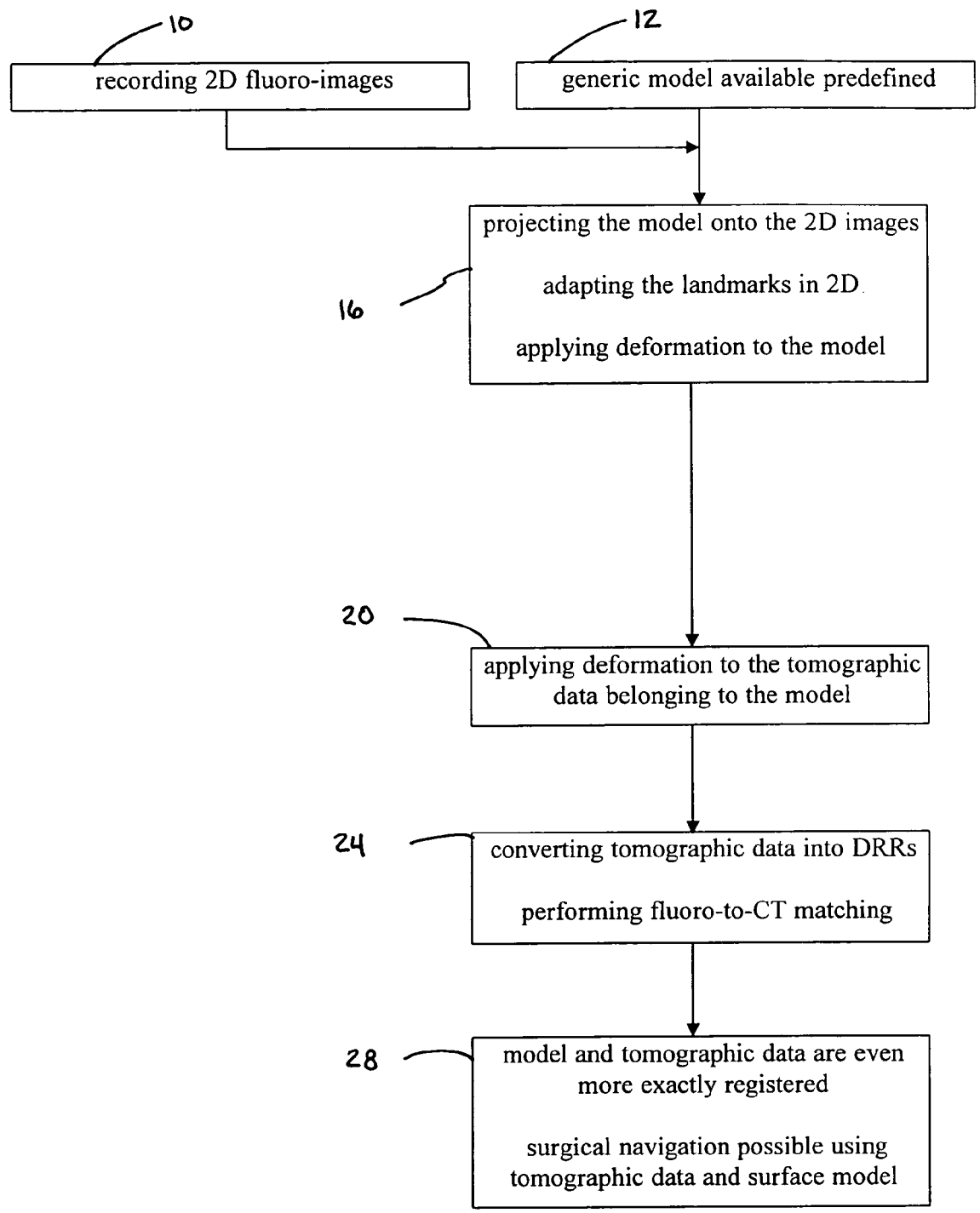
FIG. 1 is a flow diagram illustrating a method for registering and adapting a generic model in accordance with the invention.

In accordance with one aspect of the invention, the current position of a patient or a part of a patient's body and the positions of medical treatment devices or treatment-assisting devices can be detected in such navigation methods by means of a position detection unit, and the detected positional data can be assigned to body structure data, in order to jointly use the body structure data in assignment with the positional data, within the context of assisting the treatment. Such a navigation system is described for example in DE 196 39 615 C2 and corresponding U.S. Pat. No. 6,351,659, which is incorporated herein by reference in its entirety.

In accordance with one aspect of the invention, the invention is directed to a method for computer-assisted medical navigation and/or pre-operative treatment planning. The method can avoid producing a separate image data set, which is cost-intensive and a burden to health, for navigation/treatment planning, while nonetheless providing sufficiently accurate navigation.

In accordance with one aspect of the invention, in a computer-assisted medical navigation method and/or treatment planning method, body structure data is used. The body structure data can be obtained based on a generic model, which has been adapted by linking it with patient-characteristic detection data, such as pre-operatively or intra-operatively obtained x-ray image data.

If the x-ray image data includes more than one image from different directions of projection, then these two-dimensional summation images can be in a known or calculable navigational relationship to each other.

On the basis of this known relationship, a three-dimensional generic model is superimposed onto the patient-specific x-ray images, and a projection of this model is adapted to the respective x-ray images. The model can be adapted in two-dimensional space, unlike other described methods, which employ two-dimensional patient-specific data to create a three-dimensional model.

When adapting in this way, the projection of anatomic landmarks or geometries, such as the edges of bones or typical osseous borders and anatomical structures (for example, the processus transversus and spinosus of a vertebra, or the projected course of the pedical in a vertebra model), are automatically or manually identified. Projecting the stored model structures is then adapted to these two-dimensionally identified landmarks.

This adaptation requires a guideline for transforming the model onto the patient-specific data, which also enables the information stored in the model, for example, a CT or MR data set, to be appropriately modified, such that a "virtual" data set of the patient, including tomographic images, can be used for navigation.

By calculating the projection, this data set can be displayed as digital reconstructed radiography (DRR) and compared with the patient-specific data in order to automatically or manually verify the model.

In one embodiment, two transillumination images are sufficient. It is advisable to record these perpendicular to each other, such as, for example, in the case of anterior-posterior and lateral images, though other angles are not a problem. Other transillumination images can, however, also be incorporated in order to make the model more precise.

In one embodiment, the generic model is pre-defined. It can contain information on the deforming models used and their interrelationships, as well as landmarks or other points of interest, which can be used to deform the model. The model can include either a surface model or a tomographic data model or a combination of both. One advantage of the surface model is that it is simple and quick to deform, which makes it particularly suitable for real-time applications. Tomographic data models are required for specific visualization and provide extended information on the volume of a structure.

In order to use the three-dimensional model in conjunction with the transillumination images, it has to be adapted ("morphed") to the information of the images. In one embodiment, the landmarks and other points of interest, which are used for deforming, are projected onto the two-dimensional transillumination images. The deformation of the model is defined by adjusting the predetermined landmarks to the contour of the desired structure.

The landmarks do not have to be identified in more than one transillumination image. The prerequisite that at least two images are required in order to establish the position of the landmarks, as is required in the prior art, does not apply to the method described herein. It is sufficient if the landmarks are placed in just one of the images. Contrary to the conventional method as set forth in DE 100 37 491 A1, a rough model is not produced from the projections, since the model in the method in accordance with the invention is predefined and, therefore, can be optimized for precise displaying. The number of landmarks to be identified is also substantially lower than in the method as set forth in WO 99/59106. For the example of the spine, at most, 20 landmarks are required.

The tomographic image data can be predefined together with the model, and further pre-operative tomographic imaging does not have to performed.

Since the model used represents a predefined reference of the structure to be visualized, it only has to be adapted to the transillumination images. One advantage for the surgeon is that he obtains a precise 3D representation of the desired structure, irrespective of the number of transillumination images and without having to fall back on elaborate and costly tomographic image data (MR).

In methods such as those described in the specifications of DE 100 37 491 A1 and WO 99/59106, the precision in registering the desired structure is dependent on placing the landmarks and/or identifying the contour in the transillumination image. In the method in accordance with one embodiment of the invention, this error can still be minimized. To this end, the transillumination data predefined with the generic model are used. The deforming guideline, generated from the information of the transillumination images, is then applied to the tomographic data. A tomographic image data set, adapted to the patient, can be obtained. Using a fluoro-to-CT matching algorithm, the deformed tomographic image data set can then additionally be registered. This minimizes inaccuracies that can arise from manually or automatically placing the landmarks. With the aid of this step, the precision of the method can be substantially increased and reliability can also be improved. The precision of the fluoro-to-CT matching method has been demonstrated in a number of studies, and the results of this algorithm are easily verified.

When "navigation" is mentioned in the following, this term is intended in principle to also include pre-operative treatment planning in the context of which a surgeon determines an ideal approach for a treatment beforehand, for example, manually determines and fixes the ideal position of an implant.

The advantages of the present invention are based, among other things, on the fact that by using a generic model adapted to the patient, it is no longer necessary to produce a separate data set for the body structure, for the treatment for which medical navigation is to be provided. This spares the patient the radiation load as well as saves the costs of producing the data set (for example, by tomography). In addition, linking the generic body structure data with patient-characteristic detection data provides a data set which enables highly accurate medical navigation. The generic model, which can be a kind of universal model for the body structure in question, for which all the relevant data is available, does not include data tailored specifically to the patient in question, but does include sufficient anatomical and/or body structure data to be able to provide a sufficiently accurate basis for medical navigation, once it has been adapted with the aid of patient-characteristic detection data.

It is possible within the framework of the present invention to provide the body structure data in the form of an image data set, such as a tomographic imaging data set.

In this way, separate image detection data sets are not generated, as in methods in accordance with the prior art. Rather, the generic model itself is already provided in the form of an image data set, which can then be adapted to the respective patient, to obtain an image data set that is valid for the patient. The image data set is adapted by way of superimposing, for example, patient-specific x-ray images, which represent a two-dimensional summation image from a defined direction of projection, and projecting the three-dimensional generic model onto said summation image.

The projection of the model onto the patient-specific data is adapted using knowledge of the three-dimensional, model-specific interdependence between anatomical landmarks and structures. Thus, manual or automatic shaping between the model and the patient data can, depending on the structure, correspond to shifting, deforming or rotating the model, or to a combination of these.

The deforming, shifting or rotating guideline thus obtained for the model can then be applied to the information stored in the model, to generate a three-dimensional image data set or to deform an already existing image data set with the aid of the guideline.

This image data set can then be employed just like one produced cost-intensively and with pre-operative radiation load for the patient. It is conceivable, for example, to use a generic model comprising a typical or average body structure, for example, a simple model representation of a vertebra, humerus, radius or ulna, femur, tibia or pelvic bone, or another osseous body structure.

The generic model can also include a statistical model of the body structure, such as one based on statistical evaluations of an indefinite number of image data sets, for example, of actual vertebra image data sets.

Furthermore, the possibility exists of providing the generic model directly as a kind of model package for a multitude of body structures of the same type. In this case, it is possible when adapting the model to isolate from the multitude of models in the package the one that best matches the patient-characteristic detection data, such that the model only has to be slightly adapted with computer assistance.

Within the framework of the present invention, the generic model can include a two- or three-dimensional data set of a body structure, also a geometric model. In other words, the generic model can include both three-dimensional data (for example, a vertebra model) and two-dimensional data (for example, virtual x-ray images) or also a model in the form of geometric data. This data can, for example, be angles and/or trajectory information, which can be displayed for the physician and indicate to him the ideal position of an implant.

Various types of patient-characteristic data are outlined in the following, such as can be used for adapting the generic model. It is also always possible to employ combinations of such data, referred to as diagnostic data in the following, to this end.

The patient-characteristic data can be x-ray data, from x-ray images produced before or during treatment, such as bi-planar or multi-planar x-ray images. An example of this is when x-ray images of the patient are already available, which were produced within the context of previous examinations. Data about body structures from these "old" x-ray images is particularly suitable if deviations of form with respect to the generic model are to be calculated in.

It is, however, also possible, even during treatment, to produce individual x-ray images of the patient and to include this information in adapting the generic model. The advantage as compared to conventional "x-ray navigation" is then that it is not necessary to produce a large multitude of x-ray images, such as are used in navigation based on x-ray images. It is sufficient for adapting the generic model to produce just one or very few x-ray images, which, moreover, can be restricted to a very small section of the body. This significantly reduces the radiation load as compared to conventional x-ray navigation.

The above applies in the same way to computer tomography or nuclear spin tomography image data. Data may be used, which is derived from tomographic images produced much earlier, but whose information is sufficient for suitably adapting the generic model.

Moreover, the diagnostic image data can also be digitally reconstructed x-ray image data (DRRs=digitally reconstructed radiographs), which can, for example, be produced from tomographic image data sets already available, without the patient again having to be subjected to x-ray imaging.

It is, however, not absolutely necessary to use complicated, patient-characteristic detection data and/or diagnostic data in this way, to be able to adapt the generic model sufficiently. It can be sufficient to use acquired point-positional information of the patient's body structure, such as natural or artificial landmarks. The patient-characteristic diagnostic data can then, for example, be the distance between two landmarks (for example, apophyses), which alone can give sufficient information about how the generic model should be restructured. Similarly, data on size, weight or lengths of the body section or of one or more limbs of the patient can be used as a basis for this.

The generic model can be adapted within the context of the invention using one or more of the following methods: manually adapting with the assistance of image representation, such as by offsetting points and landmarks or by shifting, rotating, stretching or compressing the generic model on a screen output by means of user-interface means; automatic image fusion methods, for example, based on automatically identifying particular anatomical features; and registering and/or fusing image data of the generic model, such as digitally reconstructed x-ray images, and the same from computer tomography or nuclear spin tomography image data sets.

The generic model can thus be fused using diagnostic methods either automatically, for example, by automatically identifying particular anatomical features critical for fusion, or manually, for example, by shifting, rotating and/or stretching. When the generic model is fused with actual patient information by acquiring an indefinite quantity of point information on the patient (landmarks), it is possible to use a so-called surface-matching method, i.e., a computer-assisted image adapting method, to fuse the image data. From the various methods described above, capturing the diagnostic data and adapting the generic model are combined in accordance with one embodiment of the invention, such that alongside the diagnostic data (for example, x-ray images acquired intra-operatively), additional points on the patient are also recorded, in the form of landmarks or randomly acquired points, and used to detect and adjust the position of the model or its form even more accurately, so as to enable more accurate navigation.

A hip-thigh arrangement (pelvis/femur) can also be registered by means of registered x-ray images and a generic model. The hip could then be registered, for example, by assigning landmarks between the generic model and one or more x-ray images (fluoroscopy, for example at an angle of 30°) by mathematical coupling.

Generally speaking, the positional data obtained while determining the patient-characteristic detection data, such as by acquiring landmark positions or by x-ray imaging registered in the navigation system, can be used to register the adapted body structure data in the navigation system and to visually display or introduce treatment devices and/or treatment-assisting devices in their registration to the adapted body structure. In other words, the step of capturing the diagnostic data is also simultaneously used in this way to register the patient and the adapted generic model for navigation. As long as the data of the model is fused with registered data, i.e., data which is clearly determined in the spatial position, such as registered fluoroscopy images of an x-ray navigation software, or the data of the model are registered with landmarks, or a combination of the two methods, these can be used for computer-assisted surgery and, for example, for minimally invasive operations in which instruments or implants are displayed in relation to a fused model.

The method described herein can be used both to assist in surgery in which the surgeon is provided with navigating aids on screens, and within the context of radiotherapy and/or radiosurgery. Navigation can be based on optical tracking or on magnetic tracking.

The present invention can include a program which, when running on a computer or loaded on a computer, causes the computer to perform one or more of the methods described above, and a computer program storage medium comprising such a program.

In summary, it may further be stated with respect to the above invention that it reduces the radiation load and eliminates or at least minimizes the costs of tomographic imaging methods, and that it also has the advantage as compared to pure x-ray navigation that it enables the surgeon three-dimensional navigation and orientation. Further advantages lie in the fact that the steps resulting in the patient being registered are substantially less complicated and the patient can be registered using few manual steps. Costly diagnostic examinations are simplified, and acquiring points/landmarks on the patient for registering can also be made superfluous, if already calibrated data (for example, registered x-ray data) are used and additional useful information is obtained through fusion with the generic model (for example, converting a quantity of two-dimensional information into actual three-dimensional information).

It is thus possible in accordance with the invention to automatically display the ideal position of implants or instruments at little cost, such that surgery can be performed more quickly, more securely, and less invasively.

With reference now to FIG. 1, a flow chart illustrating a method for registering and adapting a generic model is provided. It is to be appreciated that the method illustrated in FIG. 1 is described in greater detail above. The method can include recording one or more two-dimensional fluoro-images at step 10 and selecting a predefined, available generic model at step 12. Step 16 can include projecting the generic model on the two-dimensional images, adapting landmarks in the two-dimensional images, and applying the appropriate deformation to the generic model. Step 20 can include applying deformation to the tomographic data belonging to the generic mode. Step 24 can include converting tomographic data into DRRs and performing fluoro-to-CT matching. At step 28, a model and tomographic data, which are more exactly and/or precisely registered, results. This makes surgical navigation possible using, for example, the tomographic data and a surface model.

FIGS. 2-6 show screen shots of a computer application, which assists the method described herein, in accordance with one embodiment of the invention. Screen shots for two-dimensionally superimposing x-ray images and projections from generic models may be recognized, including highlighted landmarks of the model, which are placed on the corresponding points of the patient x-ray images by the operator, so as to ascertain a suitable transformation.

Figure 2:
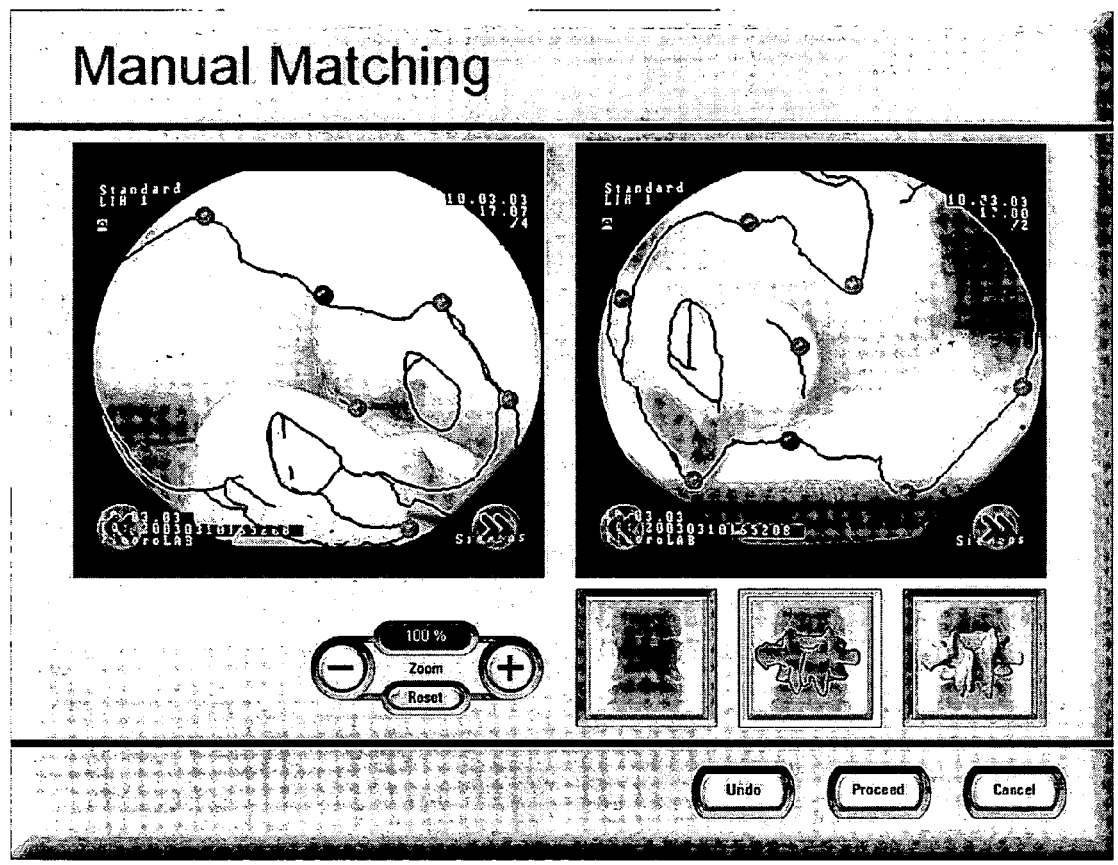
FIGS. 2 to 6 are exemplary screen shots of a computer application which assists the method in accordance with the invention.
Figure 3:
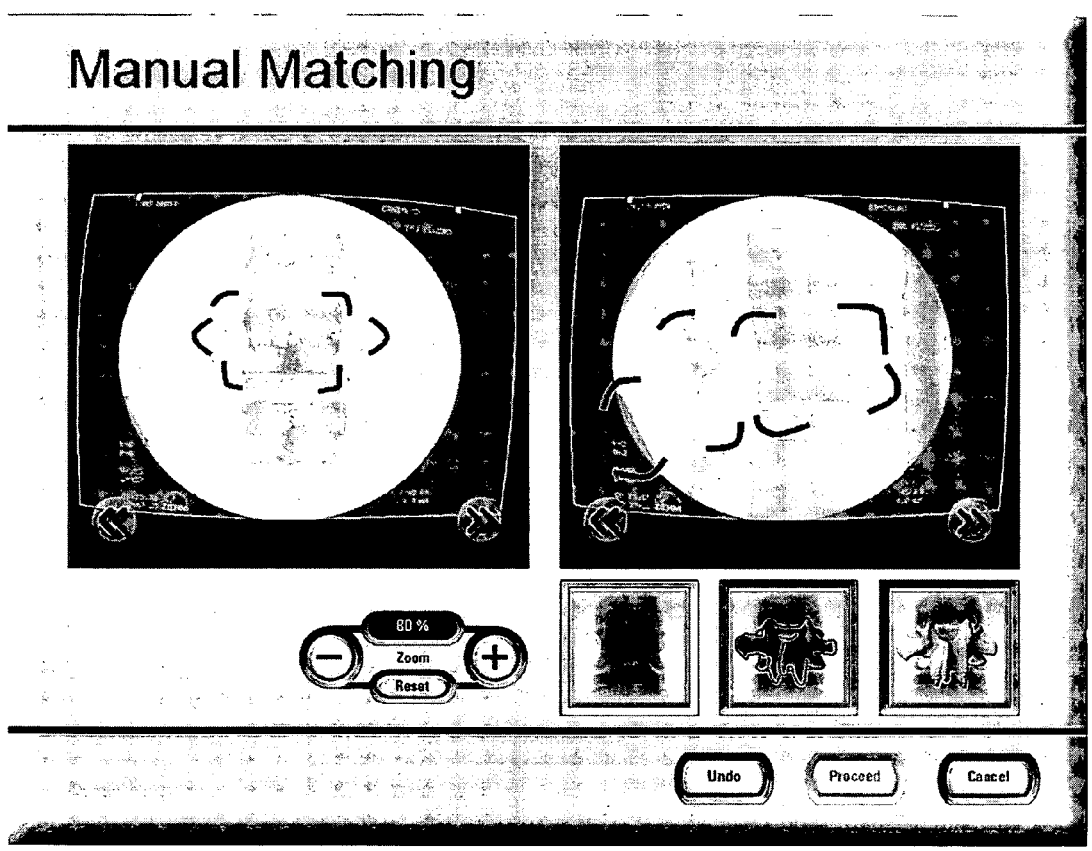
Figure 4:
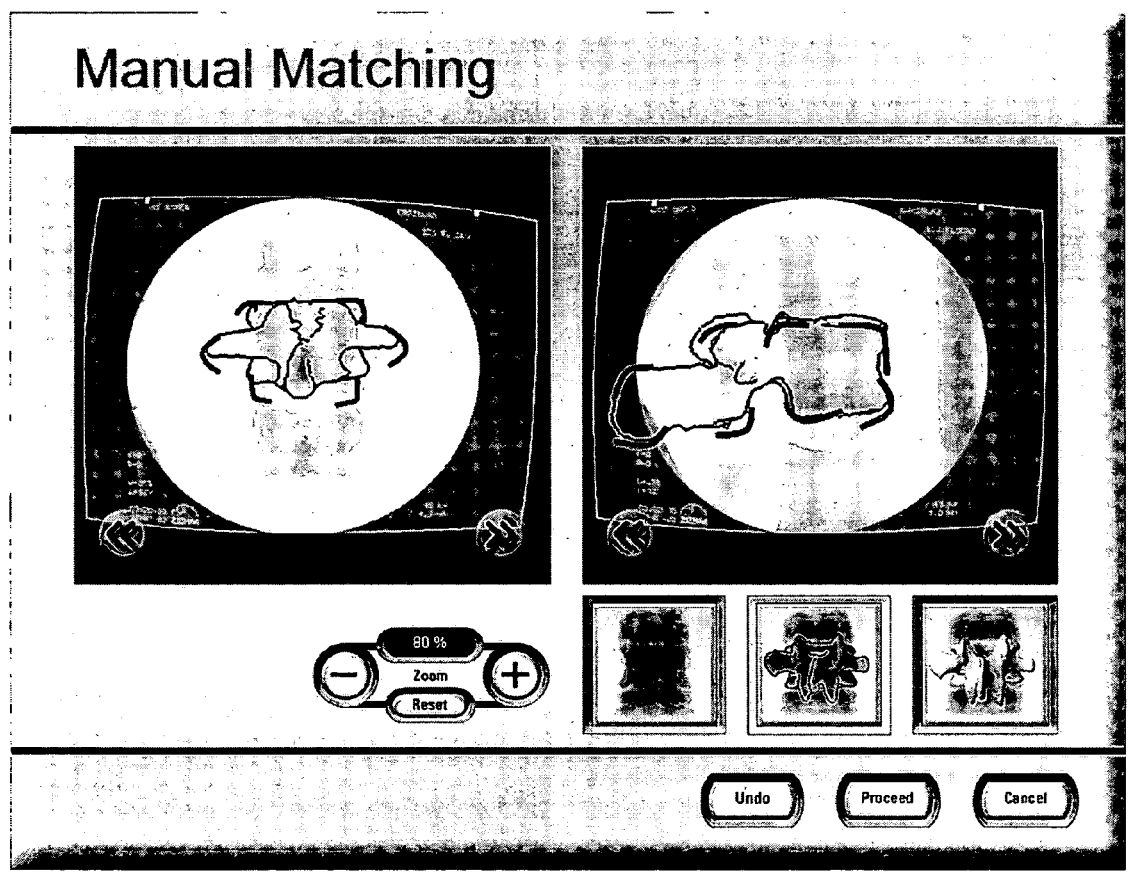
Figure 5:
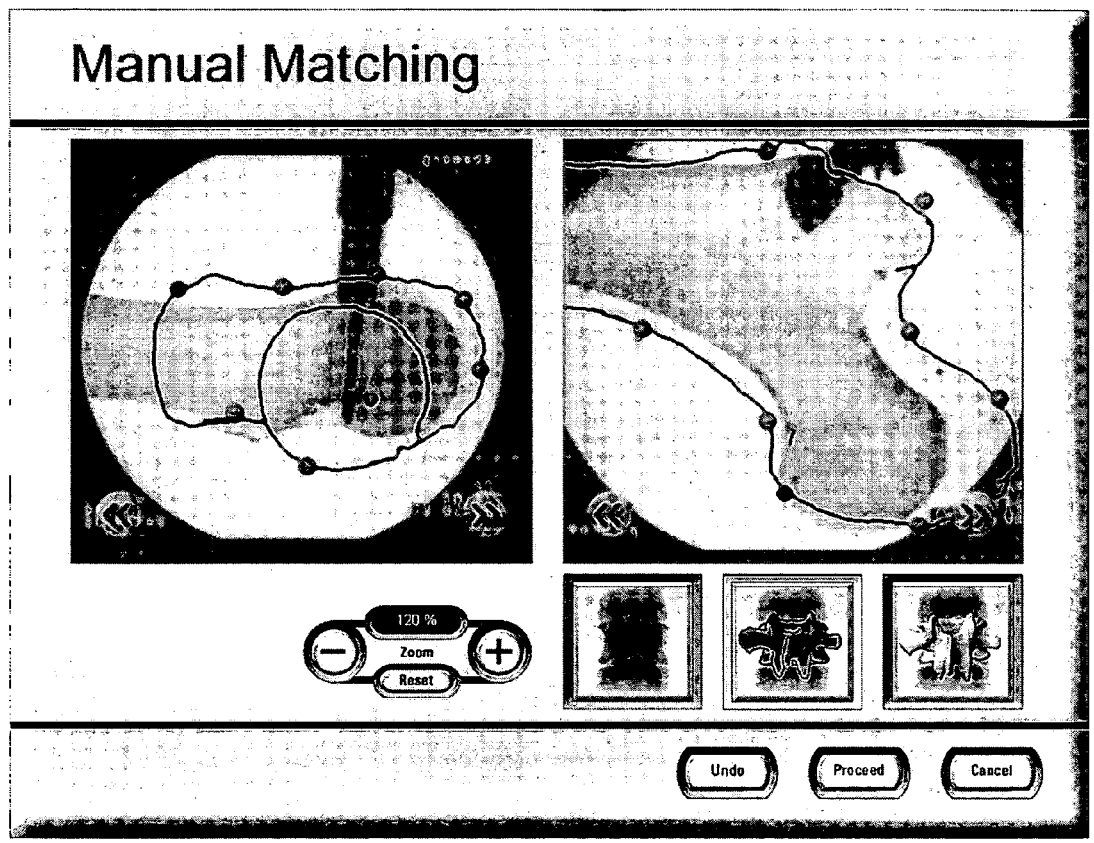

FIG. 2 shows two exemplary views of a hip model, while FIGS. 3 and 4 show two exemplary views of a vertebra model, wherein only the landmarks are indicated. FIG. 5 shows exemplary views of a femur.

Figure 6:
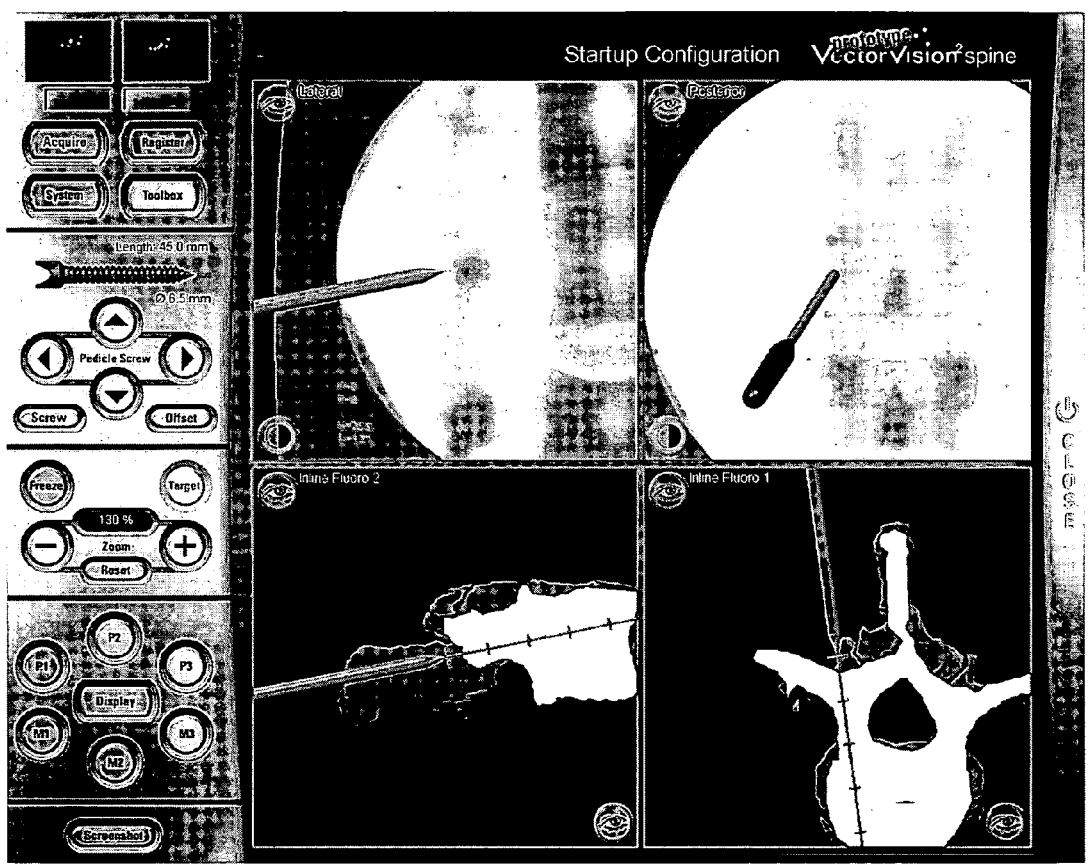

Once the transformation guideline is then ascertained and the generic model adapted, fluoro-navigation can be performed as shown in FIG. 6, on the x-ray images (top) and assisted by adapted generic 3D image representations (bottom).

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, systems, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for computer-assisted medical navigation, said method comprising:

during a medical treatment procedure, detecting a position of a patient or a part of the patient's body with the patient being in position for treatment, and without removing the patient from the position for treatment, acquiring patient-characteristic, two dimensional detection data;

detecting a position(s) of at least one medical treatment device or treatment-assisting device;

creating patient-specific body structure data, wherein creating the patient-specific body structure data includes:

projecting a three-dimensional generic model onto the acquired patient-characteristic, two-dimensional detection data, adapting the projection(s) of the three-dimensional generic model to the the patient-characteristic, two-dimensional detection data, and adapting the three-dimensional generic model to conform to the adapted projection(s) of the three-dimensional generic model; and assigning the detected position(s) of the patient and/or the at least one medical treatment device or treatment-assisting device to the created patient-specific body structure data.

2. The method as set forth in claim 1, further comprising:

jointly using the body structure data and assignment with the detected positional data within the context of assisting the navigation or treatment planning.

3. The method as set forth in claim 2, said method including:

obtaining positional data while determining patient-characteristic detection data, said obtaining including at least one of (i) acquiring landmark positions, and (ii) registering x-ray imaging in a navigation system;

using the obtained positional data to register the adapted body structure data in a navigation system, and visually displaying or using treatment devices or treatment-assisting devices in their registration to the adapted body structure.

4. The method as set forth in claim 1, wherein the body structure data is provided in the form of a tomographic image data set.

5. The method as set forth in claim 1, wherein the generic model includes at least one of (i) a typical or average body structure; (ii) a statistical model of said body structure based on statistical evaluations of an indefinite number of image data sets; (iii) a multitude of body structures of the same type; and (iv) a two- or three-dimensional data set of a body structure and a geometric model.

6. The method as set forth in claim 1, wherein the patient-characteristic data is diagnostic data obtained from the patient, which includes at least one of:

(i) x-ray image data from bi-planar or multi-planar x-ray images produced before or during treatment;

(ii) computer tomography or nuclear spin tomography image data;

(iii) digitally reconstructed x-ray image data;

(iv) acquired point-positional information of the patient's body structure; and (v) data on size, weight or lengths of the body section or one or more limbs of the patient.

7. The method as set forth in claim 6, wherein the acquired point-positional information of the patient's body structure includes natural or artificial landmarks.

8. The method as set forth in claim 1, wherein creating patient-specific body structure data includes:
manually adapting with the assistance of image representation.

9. The method as set forth in claim 8, wherein the manually adapting includes one of (i) offsetting points and landmarks on a screen output using a user-interface means, and (ii) shifting, rotating, stretching or compressing the generic model on a screen output using a user-interface means.

10. The method as set forth in claim 1, wherein creating patient-specific body structure data includes:
automatic image fusion by automatically identifying particular anatomical features.

11. The method as set forth in claim 1, wherein adapting the three-dimensional generic model includes:
registering and/or fusing digitally reconstructed x-ray images of the generic model and digitally reconstructed x-ray images from computer tomography or nuclear spin tomography image data sets; and
calculating the adapted body structure data using computer-assistance.

12. The method as set forth in claim 1, further comprising:
superimposing the three-dimensional generic model with patient-specific x-ray images; and
adapting a projection of the model to the respective x-ray images.

13. The method as set forth in claim 12, wherein anatomic landmarks or geometries projected into the patient-specific x-ray images are automatically or manually identified, and projected model structures are adapted to the two-dimensional landmarks.

14. The method as set forth in claim 13, wherein the model is adapted using a transformation guideline which also enables information stored in the model to be appropriately modified, such that a data set of the patient consisting of tomographic images can be used for navigation.

15. The method as set forth in claim 14, further comprising:
displaying the patient data set as a digital reconstructed radiograph (DRR); and
comparing the patient data set with the patient-specific data to automatically or manually verify the model.

16. The method as set forth in claim 15, wherein the image data set is adapted by way of superimposing patient-specific x-ray images which represent a two-dimensional summation image from a defined direction of projection, and projecting the three-dimensional generic model onto said summation image.

17. The method as set forth in claim 16, wherein a deforming and rotating guideline obtained for the model is applied to the information stored in the model to generate a three-dimensional image data set or to deform an already existing image data set with the aid of said guideline.

18. The method as set forth in claim 16, wherein a deforming, rotating, and translational guideline obtained for the model is applied to the information stored in the model, to generate a three-dimensional image data set or to deform an already existing image data set with the aid of said guideline.

19. A non-transitory computer-readable medium comprising computer executable instructions adapted to perform the method in accordance with claim 1.

20. The method as set forth in claim 1, wherein creating patient-specific body structure data includes:
registering and/or fusing digitally reconstructed x-ray images of the generic model with intra- or pre-operative x-ray images to obtain adapted body structure data; and
calculating the adapted body structure data using computer-assistance.

21. The method as set forth in claim 1, further comprising:
superimposing patient-specific x-ray images with the three-dimensional generic model; and
adapting a projection of the model to the respective x-ray images.

22. A method for computer-assisted medical navigation, said method comprising:
during a medical treatment procedure, detecting a position of a patient or a part of the patient's body with the patient being in position for treatment, and without removing the patient from the position for treatment, acquiring patient-characteristic, two-dimensional detection data;
detecting a position(s) of at least one medical instrument or treatment-assisting device;
creating patient-specific body structure data, wherein creating the patient-specific body structure data includes:
projecting a three-dimensional generic model onto the acquired patient-characteristic, two-dimensional detection data,
adapting the projection(s) of the three-dimensional generic model to the patient-characteristic, two-dimensional detection data, and
adapting the three-dimensional generic model to conform to the adapted projection(s) of the three-dimensional generic model,
wherein the generic model includes a statistical model of the body structure based on statistical evaluations of a number of image data sets; and
assigning the detected position(s) of the patient and/or the at least one medical treatment device or treatment-assisting device to the created patient-specific body structure data.

* * * * *